United States Patent [19]

Holmstrom et al.

[11] 4,419,885

[45] Dec. 13, 1983

[54] METHOD OF VERIFYING THE STRESS ROLLING OF A METALLIC RIM

[75] Inventors: Roy C. Holmstrom, Lake Orion; John V. Liggett, Plymouth, both of Mich.

[73] Assignee: Rockwell International Corporation, Pittsburgh, Pa.

[21] Appl. No.: 379,397

[22] Filed: May 18, 1982

[51] Int. Cl.³ .............................................. G01N 3/40
[52] U.S. Cl. ........................................ 73/78; 72/31; 73/87; 73/432 R
[58] Field of Search ................... 73/78, 79, 81, 82, 83, 73/85, 87, 432 Z; 72/31, 32

[56] References Cited

U.S. PATENT DOCUMENTS 2,527,612 10/1950 Youngblood ........................ 73/78
2,559,016 7/1951 Grossmann ........................ 73/78

*Primary Examiner*—S. Clement Swisher

[57] ABSTRACT

A method of verifying the stress rolling of a metallic rim includes the steps of taking a first hardness reading of the surface that is to have been stress rolled, taking a second hardness reading of a reference surface that has not been stress rolled and comparing the readings so that the first hardness reading will be significantly higher than the second only if the surface has been stress rolled.

3 Claims, 2 Drawing Figures

METHOD OF VERIFYING THE STRESS ROLLING OF A METALLIC RIM

BACKGROUND OF THE INVENTION

1. Field of the Invention

This invention relates to an improved method of verifying the stress rolling of a surface of a metallic rim and, more specifically, one which includes taking and comparing hardness readings of the surface and a reference surface which has not been stress rolled.

2. Description of the Prior Art

It is well known that metallic rims of vehicle wheels or the like can be stress rolled to enhance the fatigue life of the rim which is being subjected to cyclical tensile stresses. Generally, this is accomplished by applying a compressive force to the rim in the portion thereof to be strengthened in a direction which is generally perpendicular to the direction of the tensile stresses produced therein. The application of the compressive force in this area will produce a compressive stress within the portion of the rim which is in the opposite direction to the eventual tensile stress. It has been found that "pre-stressing" in this manner enhances the fatigue life of such a rim which, during normal use, is expected to be repeatedly subjected to cyclical tensile forces.

However, although the stress rolling operation is most desirable in the formation of a vehicle wheel, there are problems concerning verification after the stress rolling has been accomplished. Vehicle wheels may be made of any number of materials such as aluminum, steel or other alloy materials. The initial material used to form the wheel may be purchased under broad specification requirements so that the material may have a general hardness or surface characteristics which fall within a fairly wide range of acceptable limits. Additionally, at various stages in the wheel production, the particular material may be subjected to heat treating or quenching or may be cold worked generally to improve its characteristics.

In any case, the process of stress rolling does not necessarily alter the surface condition of the metallic rim sufficiently to allow verification simply by visual inspection. It is, therefore, possible for the stress rolling operation to be omitted or inadequately performed and for a particular wheel to be otherwise properly manufactured for sale without having the desired stress rolling feature. Accordingly, there remains a need for a method of verifying that the desired stress rolling operation has been accomplished on a metallic rim at various stages in the manufacture of a wheel or prior to final release from production.

SUMMARY OF THE INVENTION

It is, therefore, an object of this invention to provide a method of verifying the stress rolling of a surface of a metallic rim.

These and other objects of the invention are provided in a preferred embodiment thereof including a method of verifying that a surface of a portion of a metallic rim has been stress rolled, which metallic rim includes a reference surface that has not been stress rolled. The method includes taking a first hardness reading of the surface and taking a second hardness reading of the reference surface. The first hardness reading is compared to the second hardness reading and the first hardness reading would be significantly higher than the second hardness reading when the surface of the portion of the metallic rim has been stress rolled and would not be significantly higher than the second hardness reading if the surface has not been stress rolled.

DETAILED DESCRIPTION OF THE PREFERRED EMBODIMENT

Figure 1:
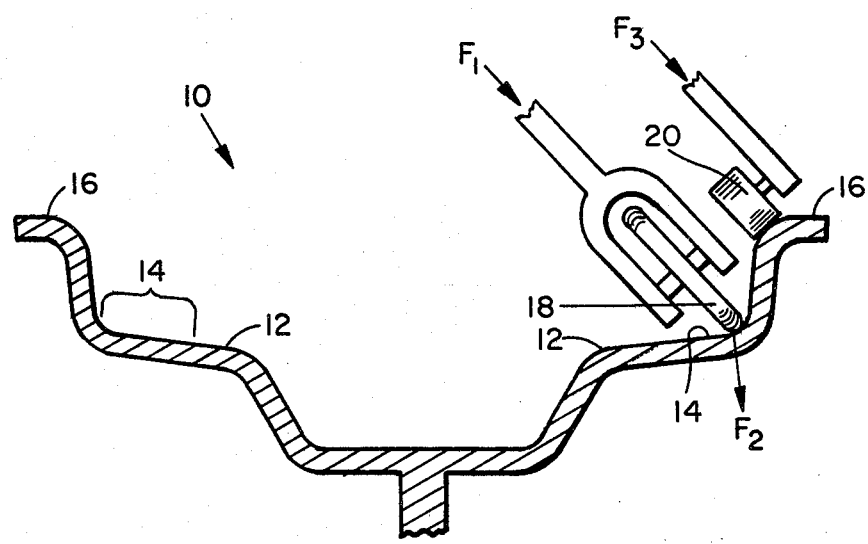
FIG. 1 shows a sectional profile of a typical vehicle wheel rim being stress rolled.

As seen in FIG. 1, a vehicle wheel rim 10 is of the type which may be found on any number of automobiles or trucks. Although the present invention would be applicable for the verification of the stress rolling of other types of metallic rims, the vehicle wheel rim 10 can be utilized to demonstrate the various features of the invention.

For example, in the manufacture and use of such vehicle rims, there is a concern that the normal loading and operation of the vehicle produces cyclical tensile stresses within the rim which can significantly effect the life of the rim and cause eventual fatigue failure in the generally axially extending section 12 of the rim 10. Specifically, a portion 14 of the section 12 adjacent each of the radially extending peripheral flanges 16 is subjected to tensile stresses at and near the tire side surface thereof because of the forces acting on the flanges 16. When a tire (not shown) is installed on the wheel and inflated with air, the tire sidewalls exert an outward force on the flanges 16 tending to axially expand the section 12 and, more significantly, establish a bending moment within the portion 14. A certain level of tensile stresses would exist in all circumferential regions of the portions 14 near the tire side surfaces thereof even if the wheel and tire were not mounted on a vehicle.

However, it has been found that when the wheel and tire are mounted on a vehicle, the regions of the portion 14 nearest the ground are subjected to higher stresses than the remaining circumferential regions of the portions 14. As the weight of the vehicle is transmitted to the ground through the tires, the sidewalls near the bottom of the tires exert a greater outward force on the flanges 16. Accordingly, as the wheel rotates, the tensile stresses at any one circumferential region of the portions 14 cycle from a basic level when the region is away from the ground to an increased level when the region is near the ground. These cyclical tensile stresses in the portion 14 near the tire side surface thereof during each revolution of the wheel results in fatigue stress which is a major cause of wheel failure. Increasing the load on the vehicle would increase the magnitude of the cyclical tensile stresses and could further shorten the fatigue life of the wheel.

Accordingly, it has been found that it is advantageous for the portion 14 to be stress rolled to produce a residual compressive stress at and near the tires side surface thereof in opposition to the tensile stresses to enhance the fatigue life in this region. As seen in FIG. 1, this is accomplished by conventional means including a stress roller 18 which is caused to apply a compressive force at the surface of the portion 14 to create the compressive stress in the outer fibers of the metal, these fibers at the tire side surface of portion 14.

Specifically, a force F1 is applied mechanically, pneumatically or hydraulically to the stress roller 18 as it traverses the surface of the portion 14 during rotation of the rim 10. The outside surface of the stress roller 18 has a smaller radius than the radius of curvature of the portion 14 adjacent the flange 16 to insure that the stress rolling operation can be extended to the curved surface thereof. Although the preferred stress roller 18 is mounted at an angle which is not directly perpendicular to the axis of the rim 10, it should be understood that this particular angle is utilized to insure that the stress roller 18 can be brought into contact with the curved surface of the portion 14 adjacent the flange 16. There is nothing in the stress rolling process which requires such an angle. In fact, the significant predetermined force F2 to be applied to the portion 14 would really be the resulting component of the force F1 which would be perpendicular to the surface being rolled.

Although the conventional stress rolling operation as described hereinabove can be satisfactorily employed to extend the fatigue life of many wheel configurations, there is an improved method of stress rolling which adds an additional feature to further enhance the quality of the compressive stress created in the portion 14. Specifically, a means is provided for applying an outside force F3 to the rim to produce a tensile stress at and near the tire side surface of the portion 14 of the rim 10 during the application of the predetermined force F2. In the embodiment shown in FIG. 1, this is accomplished by directing a separate roller 20 into contact with the flange 16 to apply a bending moment to the rim 10 in that portion 14 thereof which is being stress rolled. As the force F3 is directed against the flange 16, there is a tendency for the outer fibers of the metal in the portion 14 to be under tension. The resulting tensile stress is in a general axial direction along the surface of the portion 14 of the rim 10. As the stress roller 18 applies a compressive force F2 at the tire side surface, a compressive stress is established in the outer fibers of the portion 14. When the force F3 being applied by the roller 20 is withdrawn from the flange 16 at the completion of the stress rolling operation, the flange 16 is urged back to its original position by the fibers beneath the outer fibers which have not been provided any residual compressive stress during the stress rolling. In any case, after this improved method of stress rolling, the outer fibers have been found to have a higher value of compressive stress than could have been obtained through the conventional stress rolling operation as described hereinablve without the use of the roller 20 or the temporary tensile stresses it produces.

It should be noted that there has been no mention of the particular material used to form the wheel rim 10. In fact, vehicle wheels of aluminum, magnesium, steel and other metal alloys have been and continue to be quite common. Stress rolling the rim in such a manner, whether a method discussed hereinabove or some other method is employed, can enhance the life of a wheel whatever material is used. Because of the value of stress rolling, it would be desirable to insure at various stages in the manufacturing of a wheel that the stress rolling has been satisfactorily accomplished.

However, it is not uncommon for the stress rolling operation to be completed without visably altering the metal in the portion 14. One would not be able to verify that the stress rolling had been accomplished, much less accomplished satisfactorily, by simply visually inspecting the portion 14.

It might be expected that there would be other ways to simply verify the satisfactory completion of the stress rolling operation. For example, since stress rolling is a form of cold working, the surface hardness should be increased by the stress rolling operation. However, simply verifying that the surface has a particular hardness would not be adequate since the hardness itself is not what is important or desired by stress rolling. It would be possible for a first steel wheel to be properly stress rolled and result in a surface hardness reading which is less than a similar surface hardness reading of a second steel wheel which has not been stress rolled. The first wheel would include the desired compressive stresses, which is the actual purpose of the stress rolling, while the second wheel would not.

This may at first glance not seem possible unless one fully understands other criteria and steps employed in the manufacture of a wheel. Whatever the raw material used to form the wheel, it is obtained by the manufacture from a supplier according to predetermined specifications. However, these specifications include various ranges of acceptable limits that could result in one wheel having a surface hardness significantly higher than a second. Additionally, in the manufacture of some wheels, other steps could affect the surface hardness in a manner which is totally independent of the compressive stresses produced by stress rolling. For example, in some steel wheels, the rim could be heat treated or quenched or could be cold worked at various stages for reasons that are completely separate from and independent of the stress rolling step which significantly produces the compressive stresses needed to improve the fatigue life. Clearly, a simple hardness reading, even if one knew what material is to be used for the wheel, would not satisfactorily verify completion or effectiveness of stress rolling.

Figure 2:
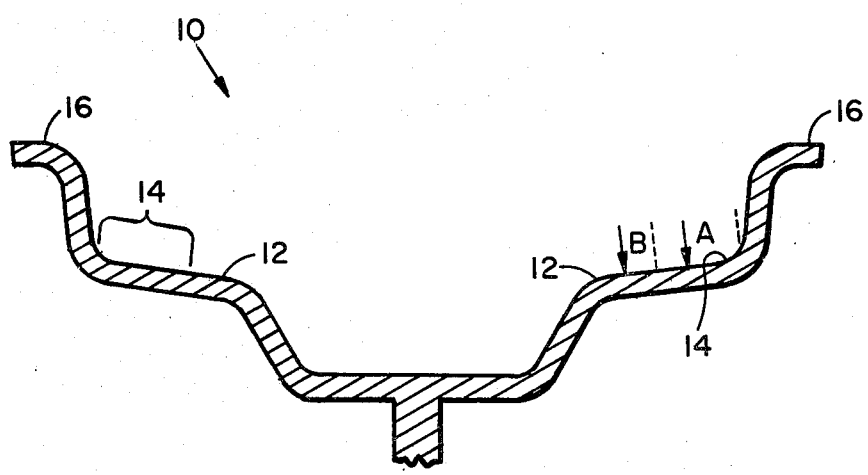
FIGS. 2 is a view of the rim shown in FIG. 1 including various features of the invention.

Therefore, it is not hardness itself which is indicative of a successful stress rolling step but an increase in hardness of the base material at the surface of the portion that has been stress rolled as compared to a reference surface of the base material in a region which has not been stress rolled. Accordingly, the present invention includes a method of verifying the effectiveness of the stress rolling operation on a metallic rim 10 as shown in a preferred embodiment thereof in FIG. 2. A hardness reading of the type well known in the metalworking art is taken at a location A on the surface of the portion 14 and at a location B at the surface of a region of the extending section 12 of the rim 10 which has not been stress rolled.

Obviously, these readings could be taken separately and then compared to insure a significant increase in hardness exists at A when compared to the hardness at B. The actual amount of increase that is desired would be determined by testing and evaluating sample wheels that have been properly stress rolled. Such tests would be expected to be conducted on each type of wheel to be manufactured to verify the effect of stress rolling on hardness for each type of raw material and each type of manufacturing process otherwise affecting hardness. It is most likely that the actual magnitude of the difference in hardness readings would not be directly used but rather a percentage difference in the basic readings.

Preferably, readings will be taken simultaneously and the testing instrument readout will be calibrated to directly read a percentage difference in the hardness readings at A and B. It is felt that this method will quickly, clearly and accurately verify the stress rolling of a metallic rim in a manner which tends to compensate for normal variations in manufacturing specifications and tolerances. Obviously, there will be alternative methods which might be employed without departing from the spirit of the invention as claimed.

We claim:

1. A method of verifying that a surface of a portion of a metallic rim has been stress rolled, said metallic rim including a reference surface that has not been stress rolled, said method comprising:

taking a first hardness reading of said surface;

taking a second hardness reading of said reference surface; and comparing said first hardness reading to said second hardness reading, said first hardness reading being significantly higher than said second hardness reading when said surface of said portion of said metallic rim has been stress rolled and not significantly higher than said second hardness reading if said surface has not been stress rolled.

2. The method of verifying as set forth in claim 1, wherein said taking of said first hardness reading and said second hardness reading are done simultaneously.

3. The method of verifying as set forth in claim 1, wherein said comparing said first hardness reading to said second hardness reading is accomplished by determining the percentage difference in said first hardness reading and said second hardness reading.

* * * * *